(12) United States Patent
Ouchi

(10) Patent No.: US 6,497,653 B2
(45) Date of Patent: Dec. 24, 2002

(54) PROBE OF ENDOSCOPE

(75) Inventor: Teruo Ouchi, Saitama (JP)

(73) Assignee: Asahi Kogaku Kogyo Kabushiki Kaisha, Tokyo (JP)

(*) Notice: Subject to any disclaimer, the term of this patent is extended or adjusted under 35 U.S.C. 154(b) by 0 days.

(21) Appl. No.: 09/902,132

(22) Filed: Jul. 10, 2001

(65) Prior Publication Data

US 2002/0032372 A1 Mar. 14, 2002

(30) Foreign Application Priority Data

Jul. 11, 2000 (JP) ......................... 2000-209899

(51) Int. Cl.⁷ ................................. A61B 1/06
(52) U.S. Cl. ......................... 600/182; 600/130
(58) Field of Search ..................... 600/130, 160, 600/182; 385/117, 118

(56) References Cited

U.S. PATENT DOCUMENTS 4,566,438 A * 1/1986 Liese et al. ............. 600/129

FOREIGN PATENT DOCUMENTS

JP 6-194582 * 7/1994 ............ G02B/6/00

* cited by examiner

Primary Examiner—John Mulcahy
(74) Attorney, Agent, or Firm—Pitney, Hardin, Kipp & Szuch LLP

(57) ABSTRACT

A probe of an endoscope comprises a light guide fiber bundle and an image guide fiber bundle. The light guide fiber bundle supplies illumination light to the distal end of the probe, to illuminate the observed object. The illumination light is reflected by the observed object, and enters the end surface of the image guide fiber bundle. When the radius of the image guide fiber bundle is a, the radius of the light guide fiber bundle is b, and the inner radius of the probe is 1, a and b satisfy the following conditions.

$$0.545 \leq a \leq 0.581$$

$$0.419 \leq b \leq 0.455$$

$$a+b=1$$

3 Claims, 2 Drawing Sheets

PROBE OF ENDOSCOPE

BACKGROUND OF THE INVENTION

1. Field of the Invention

The present invention relates to a probe of an endoscope, which has an image transmitting optical system utilizing an image guide fiber bundle, and an illumination optical system utilizing a light guide fiber bundle.

2. Description of the Related Art

Usually, a medical endoscope for observing the inside of a human body, and an industrial endoscope for observing the inside of a machine, are provided with a light guide fiber bundle and an image guide fiber bundle. Namely, the inside of the body or the machine is illuminated by the light guide fiber bundle, and an image of the observed object illuminated by the light guide fiber bundle is received and transmitted to an operation unit of the endoscope by the image guide fiber bundle. The endoscopes have a probe, which is inserted into the body or the machine and which includes a flexible tube, a bendable tube, and a distal end. Namely, the inside of the probe is essentially provided with the light guide fiber bundle, and the image guide fiber bundle.

In the light guide fiber bundle, as the illumination sectional area (i.e., the sum of the sectional area of cores of optical fibers forming the light guide fiber bundle) becomes large, the amount of illumination light which can be transmitted becomes great, and thus the observed object can be illuminated with bright light. Further, in the image guide fiber bundle, as the light receiving sectional area (i.e., the sum of the sectional area of cores of optical fibers forming the image guide fiber bundle) becomes large, the amount of light which can be received becomes great, and thus a bright image can be transmitted. Namely, if the illumination sectional area of the light guide fiber bundle is made as large as possible while the light receiving sectional area of the image guide fiber bundle is made as large as possible, the observed object can be observed as a bright object.

However, the outer diameter and the inner diameter of the probe of the endoscope are limited, because of the usage of the probe, i.e., the probe is inserted into a narrow internal space of a body, a machine etc. Further, other than the light guide fiber bundle and the image guide fiber bundle, various contents including wires for bending the bendable tube, a biopsy forceps channel and air and liquid supply tubes, in the case of a medical endoscope, for example, are housed in the probe, in which the inner diameter is limited. Therefore, the sectional area of the space, in which the light guide fiber bundle and the image guide fiber bundle can occupy, is further limited.

Furthermore, in each of the guide fiber bundles, the optical fibers are bundled and fastened in a cylindrical shape at the distal end. Therefore, the sum of the outer diameters of the guide fiber bundles should be less than the inner diameter of the probe at the distal end.

Accordingly, when accommodating the light guide fiber bundle and the image guide fiber bundle, the ends of which are fastened in a cylindrical shape, in the probe in which the sectional area of the accommodation space is limited as described above, a ratio of the illumination sectional area of the light guide fiber bundle to the light receiving sectional area of the image guide fiber bundle should be optimized so as to maximize the brightness of the observed object image.

SUMMARY OF THE INVENTION

Therefore, an object of the present invention is to provide a probe of an endoscope, in which the ratio of the outer radius of the light guide fiber bundle to the outer radius of the image guide fiber bundle is optimized.

According to the present invention, there is provided a probe of an endoscope, comprising a cylindrical tube, a light guide fiber bundle, and an image guide fiber bundle. The cylindrical tube has a distal end in which an objective lens is disposed. The light guide fiber bundle is housed in the tube. A first end portion of the light guide fiber bundle, which is positioned in the distal end, is formed in a solid cylindrical shape. The light guide fiber bundle supplies illumination light to the distal end. The image guide fiber bundle is housed in the tube. A second end portion of the image guide fiber bundle, which is positioned in the distal end, is formed in a solid cylindrical shape. The image guide fiber bundle transmits an image of an observed object obtained by the objective lens. The outer radius "a" of the second end portion and the outer radius "b" of the first end portion satisfy $0.545 \leq a \leq 0.581$, $0.419 \leq b \leq 0.455$, and $a+b=1$, wherein the inner radius of the tube is supposed to be 1.

When the outer radius "a" and the outer radius "b" satisfy $0.545 \leq a \leq 0.581$, $0.419 \leq b \leq 0.455$, and $a+b=1$, and the inner diameter of the probe is fixed, the amount of light of the observed object image transmitted by the image guide fiber bundle becomes the maximum. Therefore, even though the light guide fiber bundle and the image guide fiber bundle are inserted in the probe in which the sectional area of the inner space is limited, a bright object can be effectively obtained.

BRIEF DESCRIPTION OF THE DRAWINGS

The objects and advantages of the present invention will be better understood from the following description, with reference to the accompanying drawings, in which.

DESCRIPTION OF THE PREFERRED EMBODIMENTS

Figure 1:
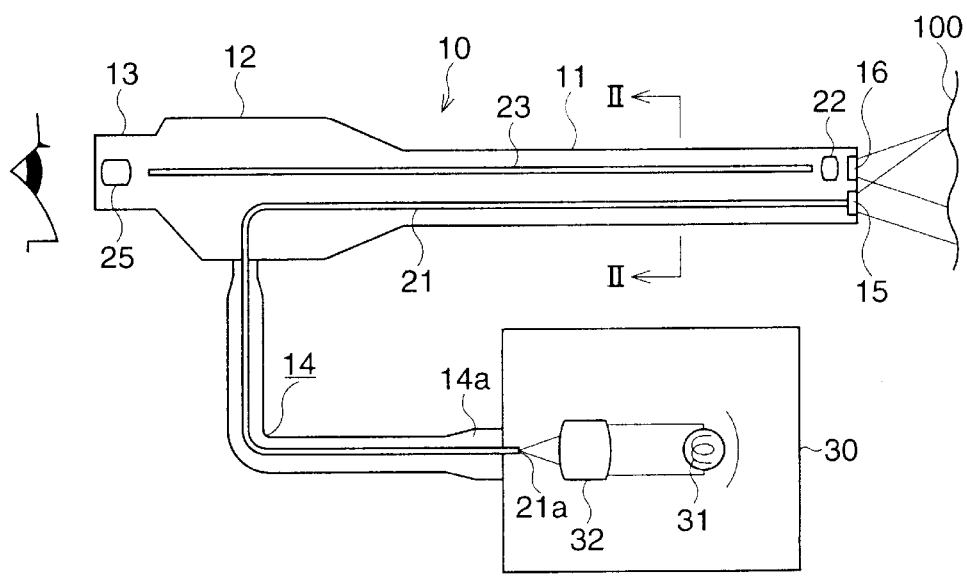
FIG. 1 is a schematic view of an endoscope system including an endoscope to which an embodiment of the present invention is applied.

The present invention will be described below with reference to the embodiments shown in the drawings.

FIG. 1 is a schematic view showing an endoscope system including an endoscope 10 to which an embodiment of the present invention is applied. As shown in FIG. 1, the endoscope system has the endoscope 10 and a light source device 30. The endoscope 10 is provided with a probe 11, which is inserted into the inside of a body or a machine, an operation unit 12 connected to an end portion of the probe 11, an eyepiece unit 13 fixed to an end portion of the operation unit 12, and a flexible light guide tube 14 projecting from a side surface of the operation unit 12.

The probe 11 is divided into a distal end located at an end thereof, a bendable tube, to which the distal end is fixed, and a flexible tube, which is located opposite to the distal end with respect to the bendable tube. At least two holes are formed in the distal end and are parallel to the longitudinal axis of the distal end. An observing window, which is a plane-parallel transparent plate 16, is fitted in the opening of the tip end of one of the holes, and a diffuser lens 15, which is a plano-concave lens, is fitted in the opening of the tip end of the other hole, in such a manner that the flat surface of the plano-concave lens faces the outside. The inside of the hole, in which the observing window 16 is fit, is provided with an objective lens 22 forming an image of an observed object 100. The bendable tube has a structure in which metal mesh and a synthetic resin tube are laminated on an outer surface of a segment formed by coaxially connecting a plurality of metal rings, and is freely bent in a predetermined direction by drawing operation wires, fixed to the end of the bendable tube, from the rear side. The flexible tube has a structure in which metal mesh and a synthetic resin tube are laminated on an outer surface of a spiral tube formed by winding a strip of metal in a spiral, and is arbitrarily bent in accordance with the external force.

An image guide fiber bundle 23 and a light guide fiber bundle 21 are inserted in the bendable tube and the flexible tube. Both the light guide fiber bundle 21 and the image guide fiber bundle 23 have a structure in which a plurality of optical fibers are bundled in a solid cylindrical shape and fastened with an adhesive agent only at the end portions, and portions other than the end portions are inserted in a silicone tube without fastening the optical fibers. One end portion of the image guide fiber bundle 23, which is fastened in the solid cylindrical shape, is inserted and fixed in the hole in which the objective lens 22 is provided at the distal end of the probe. Similarly, one end portion of the light guide fiber bundle 21, which is fastened in the solid cylindrical shape, is inserted and fixed in the hole in which the diffuser lens 15 is fitted at the distal end of the probe.

Figure 2:
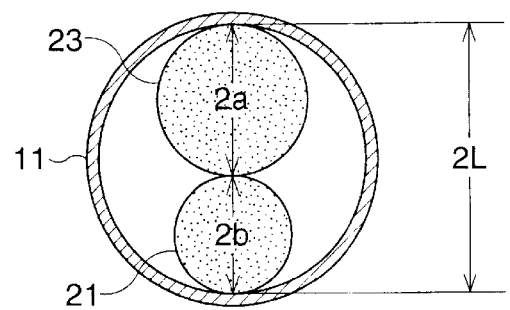
FIG. 2 is a vertical sectional view along the II—II line in FIG. 1.

FIG. 2 is a sectional view of probe 11, in which the end portion of each of the fiber bundles 21 and 23 is fastened in the solid cylindrical shape. As shown in FIG. 2, the sectional shape of each of the fiber bundles 21 and 23 in the end portions is a circle. For utilizing the internal space of the probe 11 as effectively as possible, the inside of the probe (i.e., the distal end or the bendable tube) 11 satisfies the following formula (1), wherein the diameter of the light guide fiber bundle 21 is 2b, the diameter of the image guide fiber bundle 23 is 2a, and the inner diameter of the probe 11 is 2L.

$$2a+2b=2L$$
$$a+b=L$$
$$b=L-a \quad (1)$$

Operation wires for bending the bendable tube and the contents corresponding to the functions of the endoscope 10 are inserted in the bendable tube and the flexible tube of the probe 11, the operation wires and the contents being omitted in FIG. 2. For example, in a medical endoscope, air and liquid supply tubes for cleansing an outer surface of the observing window 16, a biopsy forceps channel for leading the biopsy forceps to the end surface of the distal end, and so on, are inserted.

The operation unit 12 (FIG. 1) is provided with a pulley (not shown), to which an end portion of each of the operation wires is connected, and an operation dial, which is provided outside the operation unit 12 and is coaxially connected to the pulley. The operation dial is handled by the operator to rotate the pulley so that the operation wires are tensioned to bend the bendable tube in a desired direction.

The image guide fiber bundle 23 passes through the operation unit 12 to reach the eyepiece unit 13. In the eyepiece unit 13, an eyepiece 25 is housed through which the operator can observe an enlarged image of the observed object 100, which is transmitted to the rear end surface of the image guide fiber bundle 23. Note that, by adjusting the position of the eyepiece 25, a real image of the image transmitted onto the rear end surface of the image guide fiber bundle 23 can be formed on a predetermined plane, and the real image can be taken by a silver-halide-film still camera or a video camera.

The light guide fiber bundle 21 is inserted from the operation unit 12 into the flexible light guide tube 14, and projects from the end of the flexible light guide tube 14, to which a connector 14a is attached and detachably connected to a receptacle provided on the light source device 30. In a state in which the connector 14a is connected to the receptacle of the light source device 30, an incident end surface 21a of the light guide fiber bundle 21 projects into the light source device 30.

The light source device 30 houses a light source lamp 31 for radiating illumination light, and a condenser lens 32 for condensing the illumination light radiated from the light source lamp 31 onto the incident end surface 21a of the light guide fiber bundle 21.

In the endoscope system described above, most of the illumination light radiated from the light source lamp 31 of the light source device 30, is condensed by the condenser lens 32, and led to the incident end surface 21a of the light guide fiber bundle 21. The illumination light entering the incident end surface 21a of the light guide fiber bundle 21 is led in the probe 11 through the light guide fiber bundle 21 to the distal end, and radiated from the end face thereof. The radiated illumination light is diffused by the diffuser lens 15 to illuminate the observed object 100.

A part of the illumination light, diffusedly reflected by a surface of the observed object 100, passes through the observing window 16, and is converged by the objective lens 22, so that an image of the observed object 100 is formed on the front end surface of the image guide fiber bundle 23. The image is transmitted to the rear end surface through the image guide fiber bundle 23, being divided into pixels corresponding to the optical fibers. The image of the observed object 100 transmitted to the rear end surface of the image guide fiber bundle 23 is enlarged by the eyepiece 25 and observed by the operator.

The optimum ratio of the radius b of the end portion of the light guide fiber bundle 21 to the radius a of the end portion of the image guide fiber bundle 23, in the distal end of the probe 11, is described below. For simplicity of the explanation, it is supposed that the light guide fiber bundle 21 and the image guide fiber bundle 23 can transmit light, which is made incident on the whole of the end surface of both the light guide fiber bundle 21 and the image guide fiber bundle 23. Namely, regarding the light guide fiber bundle 21, a geometrically occupied sectional area is equal to an illumination sectional area, and regarding the image guide fiber bundle 23, a geometrically occupied sectional area is equal to a light receiving sectional area. Further, it is supposed that, in the light source device 30, a luminous flux of the illumination light entering the incident end surface 21a, the distance from the diffuser lens 15 to the observed object 100, and the reflectance of the surface of the observed object 100 are always constant.

The brightness x of the observed object 100 illuminated by the light guide fiber bundle 21 having the geometrical occupied sectional area "$b^2\pi$" is $$x=b^2\pi \times M \quad (2)$$

wherein "M" is a constant representing the brightness of the observed object 100 illuminated by the illumination light passing through the light guide fiber bundle 21 having the unit illumination sectional area.

Regarding object light from the observed object 100 having the brightness X, or diffusedly reflected light from the surface of the observed object 100, the amount y of light transmitted through the image guide fiber bundle 23 is $$y = x \times a^2 \Pi \times N \quad (3)$$
$$= b^2 \pi \times M \times a^2 \Pi \times N$$

wherein "N" is a constant representing the amount of light entering the image guide fiber bundle 23 having the unit light receiving sectional area, the light being included in the object light from the observed object 100. Here, if M×N=1, and b=L−a, formula (3) is transformed to formula (4).

$$y = (L-a)^2 \Pi \times a^2 \Pi \quad (4)$$
$$= (a^4 - 2La^3 + L^2a^2)\Pi^2$$

"L" is normalized, i.e., L=1, and it is defined $y/n^2$=P. Thus, formula (4) is transformed to formula (5).

$$P = a^4 - 2a^3 + a^2 \quad (5)$$

Figure 3:
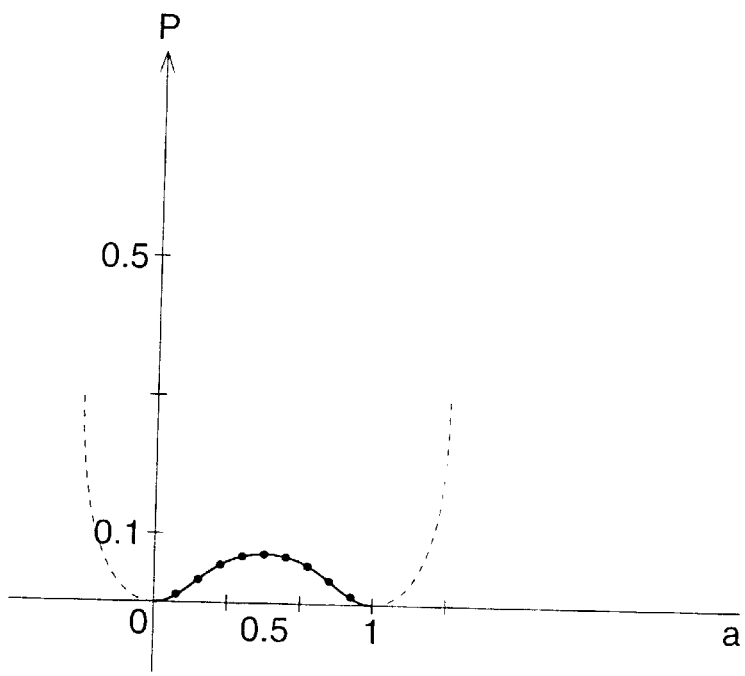
FIG. 3 is a graph showing a relationship between a radius "a" of an image guide fiber bundle and brightness of an observed object image.

Formula (5) is represented graphically as a curved line shown in FIG. 3. Note that, as understood from the relationship shown in FIG. 2 in which L is supposed to be 1, "a" is in a numerical range which is greater than 0 and less than 1. Accordingly, it is understood that "P" has a local maximum value when a=0.5. Namely, under the assumption described above, when the outer diameter 2b of the light guide fiber bundle 21 is ½ of the inner diameter 2L of the probe 11, and the outer diameter 2a of the image guide fiber bundle 23 is ½ of the inner diameter 2L of the probe 11, the brightest image can be obtained. In other words, by equalizing the sectional area of the light guide fiber bundle 21 to the sectional area of the image guide fiber bundle 23, the brightest image can be most efficiently obtained.

Figure 4:
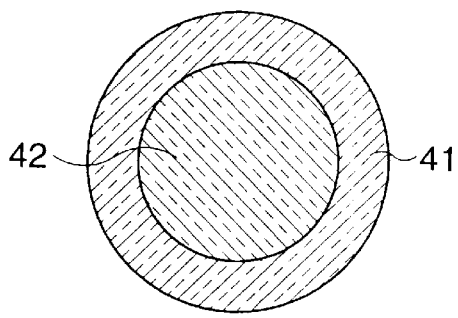
FIG. 4 is a sectional view of an optical fiber forming an image guide fiber bundle.
Figure 5:
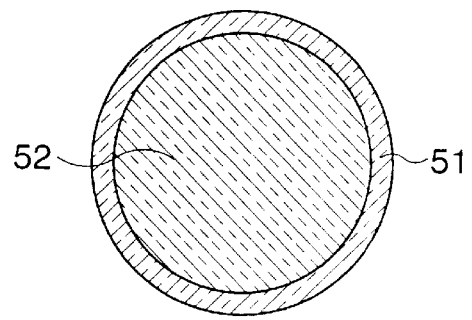
FIG. 5 is a sectional view of an optical fiber forming a light guide fiber bundle.

Note that, in reality, in the end surfaces of the fiber bundles 21 and 23, a part occupied by gaps existing among the optical fibers (the sectional areas of the gaps are directly proportional to the outer diameter of each of the fiber bundles 21 and 23), and a part occupied by cladding layers 41 (FIG. 4) and 51 (FIG. 5) of the optical fibers, cannot transmit light. Namely, in the geometrically occupied sectional area of each of the fiber bundles 21 and 23, the sum of only the sectional areas of cores 52 (FIG. 5) and 42 (FIG. 4) of the optical fibers is the actual illumination sectional area or light receiving sectional area.

Therefore, if the sum of the outer diameters of the fiber bundles 21 and 23 is made equal to the inner diameter of the probe 11 while the illumination sectional area of the light guide fiber bundle 21 (i.e., the sum of sectional areas of cores of the optical fibers) and the light receiving sectional area of the image guide fiber bundle 23 (i.e., the sum of sectional areas of cores of the optical fibers) are made equal to each other, the brightest image can be most efficiently obtained (the condition 1).

On the other hand, especially in the case of the medical endoscope, for obtaining a clear image, it is necessary that the outer diameter of each of the optical fibers should be made as small as possible so that the number of optical fibers forming the image guide fiber bundle 23 is increased. Note that for reflecting light at the interface between the core 42 and the cladding layer 41, the cladding layer 41 must have significant thickness. Therefore, conventionally, an optical fiber, in which the thickness of the cladding layer 41 is 1.5 μm and the outer diameter is 8–10 μm, is used as optical fiber forming the image guide fiber bundle 23 (see FIG. 4). Thus, a ratio of the sectional area of the core 42 to the sectional area of the whole of the optical fiber is from 39% (for the optical fiber having the outer diameter of 8 μm) to 49% (for the optical fiber having the outer diameter of 10 μm). In other words, a ratio of the sectional area of all of the optical fiber to the sectional area of the core 42 should be from 2.04 times (for the optical fiber having the outer diameter of 10 μm) to 2.56 times (for the optical fiber having the outer diameter of 8 μm) (the condition 2).

On the other hand, regarding the light guide fiber bundle 21, transmittance of light to be radiated onto the observed object is important, so a relatively thick optical fiber is used. Concretely, an optical fiber, in which the thickness of the cladding layer 51 is 2 μm and the outer diameter is 25–30 μm, is used (see FIG. 5). Accordingly, a ratio of the sectional area of the core 52 to the sectional area of the whole of the optical fiber is from 71% (for the optical fiber having the outer diameter of 25 μm) to 75% (for the optical fiber having the outer diameter of 30 μm). In other words, a ratio of the sectional area of the whole of the optical fiber to the sectional area of the core 52 should be from 1.33 times (for the optical fiber having the outer diameter of 30 μm) to 1.42 times (for the optical fiber having the outer diameter of 25 μm) (the condition 3).

Ranges of a and b satisfying the conditions 1, 2, and 3, are obtained as follows. Here, it is supposed that the geometrically occupied sectional area of the image guide fiber bundle 23 formed by the optical fibers having the outer diameter of 8 μm is $S_{I8}$, the geometrically occupied sectional area of the image guide fiber bundle 23 formed by the optical fibers having the outer diameter of 10 μm is $S_{I10}$, the geometrically occupied sectional area of the light guide fiber bundle 21 formed by the optical fibers having the outer diameter of 25 μm is $S_{L25}$, and the geometrically occupied sectional area of the light guide fiber bundle 21 formed by the optical fibers having the outer diameter of 30 μm is $S_{L30}$.

[When using the image guide fiber bundle 23 formed by the optical fibers having the outer diameter of 8 μm and the light guide fiber bundle 21 formed by the optical fibers having the outer diameter of 25 μm]

In this case, for satisfying the condition 1, a ratio of $S_{I8}$ to $S_{L25}$ should be 2.56:1.42≈1:0.55. Supposing $S_{I8}=a^2\pi 1$, $$a^2\pi = 1$$
$$a \approx 0.564 \quad (6)$$

Supposing $S_{L25}=b^2\pi=0.55$, $$b^2\pi = 0.55$$
$$b \approx 0.418 \quad (7)$$

Accordingly, when using the image guide fiber bundle 23 formed by the optical fibers having the outer diameter of 8 μm and the light guide fiber bundle 21 formed by the optical fibers having the outer diameter of 25 μm, a ratio of the radius a of the image guide fiber bundle 23 to the radius b of the light guide fiber bundle 21 should be represented by formula (8).

$$a:b = 0.564:0.418 \quad (8)$$

The values of a and b, which are in compliance with formula (8) and satisfy the relationship of a+b=1, are represented by formula (9).

$$a = 0.574$$
$$b = 0.426 \quad (9)$$

[When using the image guide fiber bundle 23 formed by the optical fibers having the outer diameter of 8 μm and the light guide fiber bundle 21 formed by the optical fibers having the outer diameter of 30 μm]

In this case, for satisfying the condition 1, a ratio of $S_{I8}$ to $S_{L30}$ should be 2.56:1.33≈1:0.520. Supposing $S_{L30}=b^2\pi=0.520$, $b_2\pi = 0.520$ $b \approx 0.407$           (10)

Accordingly, when using the image guide fiber bundle 23 formed by the optical fibers having the outer diameter of 8 μm and the light guide fiber bundle 21 formed by the optical fibers having the outer diameter of 30 μm, a ratio of the radius a of the image guide fiber bundle 23 to the radius b of the light guide fiber bundle 21 should be represented by formula (11).

$a:b = 0.564:0.407$           (11)

The values of a and b, which are in compliance with formula (11) and satisfy the relation ship of a+b=1, are represented by formula (12).

$a = 0.581$ $b = 0.419$           (12)

[When using the image guide fiber bundle 23 formed by the optical fibers having the outer diameter of 10 μm and the light guide fiber bundle 21 formed by the optical fiber shaving the outer diameter of 25 μm]

In this case, for satisfying the condition 1, a ratio of $S_{I10}$ to $S_{L25}$ should be $2.04:1.42 \approx 1:0.696$. Supposing $S_{L25} = b^2\pi = 0.696$, $b^2\pi = 0.696$ $b \approx 0.471$           (13)

Accordingly, when using the image guide fiber bundle 23 formed by the optical fibers having the outer diameter of 10 μm and the light guide fiber bundle 21 formed by the optical fibers having the outer diameter of 25 μm, a ratio of the radius a of the image guide fiber bundle 23 to the radius b of the light guide fiber bundle 21 should be represented by formula (14).

$a:b = 0.564:0.471$           (14)

The values of a and b, which are in compliance with formula (14) and satisfy the relationship of a+b=1, are represented by formula (15).

$a = 0.545$ $b = 0.455$           (15)

[When using the image guide fiber bundle 23 formed by the optical fibers having the outer diameter of 10 μm and the light guide fiber bundle 21 formed by the optical fibers having the outer diameter of 30 μm]

In this case, for satisfying the condition 1, a ratio of $S_{I10}$ to $S_{L30}$ should be $2.04:1.33 \approx 1:0.652$. Supposing $S_{L30} = b^2\pi = 0.652$, $b^2\pi = 0.652$ $b \approx 0.456$           (16)

Accordingly, when using the image guide fiber bundle 23 formed by the optical fibers having the outer diameter of 10 μm and the light guide fiber bundle 21 formed by the optical fibers having the outer diameter of 30 μm, a ratio of the radius a of the image guide fiber bundle 23 to the radius b of the light guide fiber bundle 21 should be represented by formula (17).

$a:b = 0.564:0.456$           (17)

The values of a and b, which are in compliance with formula (17) and satisfy the relationship of a+b=1, are represented by formula (18).

$a = 0.553$ $b = 0.447$           (18)

CONCLUSION

Arranging the combinations of a and b represented by formulas (9), (12), (15), and (18), when the inner radius of the probe 11 of the endoscope 10 is 1, if the radius a of the end portion of the image guide fiber bundle 23 is in a range of 0.545 and 0.581 (i.e., in a range from 0.545 to 0.581), the radius b of the end portion of the light guide fiber bundle 21 is in a range of 0.419 and 0.455, and the sum of a and b is 1 normalized by L, the image of the observed object 100 is made the brightest.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2000-209899 (filed on Jul. 11, 2000) which is expressly incorporated herein, by reference, in its entirety.

What is claimed is:

1. A probe of an endoscope, comprising:

a cylindrical tube that has a distal end in which an objective lens is disposed;

a light guide fiber bundle housed in said tube, a first end portion of said light guide fiber bundle, which is positioned in said distal end, being formed in a solid cylinder, said light guide fiber bundle supplying illumination light to said distal end; and an image guide fiber bundle housed in said tube, a second end portion of said image guide fiber bundle, which is positioned in said distal end, being formed in a solid cylinder, said image guide fiber bundle transmitting an image of an observed object obtained by said objective lens;

the outer radius "a" of said second end portion and the outer radius "b" of said first end portion satisfying $0.545 \leq a \leq 0.581$, $0.419 \leq b \leq 0.455$, and $a+b=1$ wherein the inner radius of said tube is supposed to be 1.

2. A probe according to claim 1, wherein said image guide fiber bundle is formed by bundling first optical fibers, and said light guide fiber bundle is formed by bundling second optical fibers, the sum of sectional areas of cores of said first optical fibers being equal to the sum of sectional areas of cores of said second optical fibers.

3. A probe of an endoscope, comprising:

a cylindrical tube that has a distal end;

a light guide fiber bundle housed in said tube, a first end portion of said light guide fiber bundle, which is positioned in said distal end, being formed in a solid cylinder, said light guide fiber bundle supplying illumination light to said distal end, so that said illumination light is illuminated onto and reflected by an observed object; and an image guide fiber bundle housed in said tube, a second end portion of said image guide fiber bundle, which is positioned in said distal end, being formed in a solid cylinder, said image guide fiber bundle receiving and transmitting the reflected light from said observed object;

the outer radius "a" of said second end portion and the outer radius "b" of said first end portion satisfying $0.545 \leq a \leq 0.581$, $0.419 \leq b \leq 0.455$, and $a+b=1$ wherein the inner radius of said tube is supposed to be 1.

* * * * *